US012295647B2

(12) United States Patent
Jung et al.

(10) Patent No.: US 12,295,647 B2
(45) Date of Patent: May 13, 2025

(54) HIGH DENSITY MAPPING CATHETER FOR CRYOBALLOON ABLATION

(71) Applicant: Boston Scientific Scimed, Inc., Maple Grove, MN (US)

(72) Inventors: Eugene J. Jung, San Diego, CA (US); Steven A. Kubow, Encinitas, CA (US); Rachel Lynn Troutman, Rochester, MN (US); Christopher Alan Fuhs, Roseville, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 234 days.

(21) Appl. No.: 17/087,177

(22) Filed: Nov. 2, 2020

(65) Prior Publication Data

US 2021/0128232 A1    May 6, 2021

Related U.S. Application Data

(60) Provisional application No. 62/930,245, filed on Nov. 4, 2019.

(51) Int. Cl.
*A61B 18/02* (2006.01)
*A61B 18/00* (2006.01)
*A61B 18/14* (2006.01)

(52) U.S. Cl.
CPC .......... *A61B 18/1492* (2013.01); *A61B 18/02* (2013.01); *A61B 2018/00077* (2013.01);
(Continued)

(58) Field of Classification Search
CPC ................ A61B 18/1492; A61B 18/02; A61B 2018/00077; A61B 2018/00083;
(Continued)

(56) References Cited

U.S. PATENT DOCUMENTS 10,105,179 B2    10/2018 Harley
2016/0073960 A1*   3/2016 Jung .................... A61B 5/6858
                                                  600/374

(Continued)

FOREIGN PATENT DOCUMENTS

EP           1383426 B1    12/2008

*Primary Examiner* — Jennifer Pitrak McDonald
*Assistant Examiner* — Megan T Fedorky
(74) *Attorney, Agent, or Firm* — Nelson Mullins Riley & Scarborough LLP

(57) ABSTRACT

A mapping catheter comprises a flexible shaft having a proximal end and an opposite distal end, and an expandable mapping element attached to the distal end of the shaft. The expandable mapping element is configured to self-expand from a collapsed configuration to an expanded configuration. The expanded configuration is defined by a proximal portion extending from the distal end of the shaft and forming a proximally-facing concave recess, an intermediate portion extending distally from the proximal portion and defining a maximum diameter of the mapping element when in the expanded configuration, and a distal portion having a conical shape with a distal portion diameter that decreases in a direction distally of the intermediate portion. The mapping element further includes a plurality of electrodes located in one or both of the intermediate portion or the distal portion.

10 Claims, 6 Drawing Sheets

(52) U.S. Cl.
CPC .............. *A61B 2018/00083* (2013.01); *A61B 2018/0022* (2013.01); *A61B 2018/00577* (2013.01); *A61B 2018/0212* (2013.01); *A61B 2018/0231* (2013.01); *A61B 2018/1467* (2013.01)

(58) Field of Classification Search
CPC .. A61B 2018/0022; A61B 2018/00577; A61B 2018/0212; A61B 2018/0231; A61B 2018/1467; A61B 2018/146
See application file for complete search history.

(56) References Cited

U.S. PATENT DOCUMENTS

2017/0042614 A1* 2/2017 Salahieh ............ A61M 25/1011
2017/0189106 A1* 7/2017 Schuler .................... A61B 5/00

\* cited by examiner

HIGH DENSITY MAPPING CATHETER FOR CRYOBALLOON ABLATION

CROSS REFERENCE TO RELATED APPLICATION

This application claims priority to Provisional Application No. 62/930,245, filed Nov. 4, 2019, which is herein incorporated by reference in its entirety.

TECHNICAL FIELD

The present disclosure relates generally to devices and methods for performing and assessing efficacy of cardiac ablation procedures. More particularly, the present disclosure relates to mapping devices for use in balloon cryoablation procedures.

BACKGROUND

Cardiac arrhythmias involve an abnormality in the electrical conduction of the heart and are a leading cause of stroke, heart disease, and sudden cardiac death. Treatment options for patients with arrhythmias include medications, implantable devices, and catheter ablation of cardiac tissue.

Catheter ablation involves delivering ablative energy to tissue inside the heart to block aberrant electrical activity from depolarizing heart muscle cells out of synchrony with the heart's normal conduction pattern. The procedure is performed by positioning a catheter-based energy delivery element adjacent to diseased or targeted tissue in the heart. The energy delivery element of the system is typically at or near the most distal (farthest from the operator) portion of the catheter, and often at the distal end of the device. Various forms of energy are used to ablate diseased heart tissue. These can include radio frequency (RF), balloon cryotherapy which uses cryoballoons, ultrasound and laser energy, to name a few.

Atrial fibrillation (AF) is one of the most common arrhythmias treated using balloon cryotherapy. Atrial fibrillation is typically treated by pulmonary vein isolation (PVI), a procedure that removes unusual electrical conductivity in the pulmonary vein. In the earliest stages of the disease, paroxysmal AF, the treatment strategy involves isolating the pulmonary vein(s) from the left atrial chamber. Recently, the use of balloon cryoablation procedures to treat AF has increased. In part, this stems from ease of use, shorter procedure times and improved patient outcomes. Generally speaking, balloon cryoablation entails freezing the target tissue (e.g., tissue proximate the ostia of the pulmonary veins) using a catheter-mounted cryogenic balloon. It is desirable to provide the clinician with the ability to rapidly and accurately sense intrinsic cardiac activity (or lack thereof) at or near the targeted tissue to identify ablation sites and to assess the effectiveness of the ablation energy delivery (i.e., whether the procedure has achieved conduction block). As such, there is a continuing need for improved mapping devices for use with cardiac ablation procedures, particularly balloon cryoablation procedures.

SUMMARY

In Example 1, a mapping catheter comprising a shaft having a proximal end and an opposite distal end, and an expandable mapping element attached to the distal end of the shaft. The expandable mapping element comprises a plurality of insulated members defining a three-dimensional structure when the expandable mapping element is in an expanded configuration, the plurality of insulated members including a plurality of electrode members, and a plurality of electrodes each located on a respective one of the electrode members and configured to sense intrinsic cardiac activation signals in use. The three-dimensional structure is defined by a proximal portion extending from the distal end of the shaft and forming a proximally-facing concave recess, an intermediate portion extending distally from the proximal portion and defining a maximum diameter of the mapping element when in the expanded configuration, and a distal portion having a conical shape with a distal portion diameter that decreases in a direction distally of the intermediate portion, the distal end of the shaft being axially located within the concave recess when the expandable mapping element is in the expanded configuration. The electrodes are located in at least one of the intermediate portion or the distal portion.

In Example 2, the mapping catheter of Example 1, wherein the plurality of insulated members are formed into a braided mesh structure.

In Example 3, the mapping catheter of either of Examples 1 or 2, wherein the mapping element is configured to assume a collapsed configuration when disposed within a medical device lumen, and to self-expand to the expanded configuration when extended distally from the medical device lumen.

In Example 4, the mapping catheter of any of Examples 1-3, wherein the insulated members each include a wire core made of a shape memory alloy, and an insulative covering over the wire core.

In Example 5, the mapping catheter of Example 4, wherein the wire core of each electrode member is electrically conductive and is electrically coupled to an external signal processor, and wherein each electrode is defined by an uninsulated segment of the respective one of the electrode members.

In Example 6, the mapping catheter of Example 4, wherein each of the electrodes is attached to a respective one of the electrode members.

In Example 7, the mapping catheter of Example 6, wherein the wire core of each electrode member is electrically conductive and is electrically coupled to an external signal processor, and wherein each electrode is electrically and mechanically connected to a respective one of the electrode members at an uninsulated segment thereof.

In Example 8, the mapping catheter of Example 7, further comprising a plurality of electrical conductors, wherein each of the electrical conductors is electrically and mechanically connected to one of the electrodes.

In Example 9, the mapping catheter of any of Examples 1-8, wherein the plurality of electrodes are equally spaced about the distal portion in a circular pattern when the expandable mapping element is in the expanded configuration.

In Example 10, the mapping catheter of any of Examples 1-9, wherein the plurality of electrodes includes a first group of electrodes located in the intermediate portion, and second group of electrodes located in the distal portion.

In Example 11, the mapping catheter of any of Examples 1-10, wherein the expandable mapping element includes a distal hub portion located distally of the distal portion and disposed about the plurality of insulated members.

In Example 12, the mapping catheter of any of Examples 1-11, wherein when the expandable mapping element is in the expanded configuration, the proximal portion extends radially outward and proximally relative to the distal end of the shaft, the intermediate portion extends distally of the proximal portion, and the distal portion extends distally of the intermediate portion.

In Example 13, the mapping catheter of any of Examples 1-12, wherein in the collapsed configuration, the expandable mapping element is sized to be slidably received within a lumen of a cryoablation catheter having a lumen diameter of 0.5 millimeters to 1.5 millimeters.

In Example 14, the mapping catheter of any of Examples 1-13, wherein the insulating covering is formed of a lubricious material.

In Example 15, the mapping catheter of any of Examples 1-14, further comprising a localization sensor attached to the shaft configured for sensing an electromagnetic localization field.

In Example 16, a mapping catheter comprising, a flexible shaft having a proximal end and an opposite distal end, and an expandable mapping element attached to the distal end of the shaft. The expandable mapping element comprises a plurality of insulated members formed into a braided mesh, the expandable mapping element being configured to self-expand from a collapsed configuration to an expanded configuration when extended distally from an ablation catheter lumen, the expanded configuration defined by a proximal portion extending from the distal end of the shaft and forming a proximally-facing concave recess, an intermediate portion extending distally from the proximal portion and defining a maximum diameter of the mapping element when in the expanded configuration, and a distal portion having a conical shape with a distal portion diameter that decreases in a direction distally of the intermediate portion, wherein the plurality of insulated members includes a plurality of electrode members, and wherein the distal end of the shaft is disposed within the concave recess when the expandable mapping element is in the expanded configuration. The expandable mapping element further comprises a plurality of electrodes located in one or both of the intermediate portion and the distal portion, wherein each of the electrodes is located on a respective one of the electrode members and is configured to sense intrinsic cardiac activation signals in use.

In Example 17, the mapping catheter of Example 16, wherein the insulated members each include a wire core made of a shape memory alloy, and an insulative covering over the wire core.

In Example 18, the mapping catheter of Example 17, wherein the wire core of each electrode member is electrically conductive and is electrically coupled to an external signal processor, and wherein each electrode is defined by an uninsulated segment of the respective one of the electrode members.

In Example 19, the mapping catheter of Example 17, wherein each of the electrodes is attached to a respective one of the electrode members.

In Example 20, the mapping catheter of Example 19, wherein the wire core of each electrode member is electrically conductive and is electrically coupled to an external signal processor, and wherein each electrode is electrically and mechanically connected to a respective one of the electrode members at an uninsulated segment thereof.

In Example 21, the mapping catheter of Example 16, wherein the electrodes are equally spaced about the distal portion in a circular pattern when the expandable mapping element is in the expanded configuration.

In Example 22, the mapping catheter of Example 16, wherein the plurality of electrodes includes two or more groups of electrodes each positioned at a selected axial location within one or both of the intermediate portion and the distal portion.

In Example 23, the mapping catheter of Example 22, wherein the two or more groups of electrodes includes a first group of electrodes located in the intermediate portion, and second group of electrodes located in the distal portion.

In Example 24, the mapping catheter of Example 16, wherein the expandable mapping element includes a distal hub portion distal of the distal portion and disposed about the plurality of insulated members.

In Example 25, the mapping catheter of Example 24, wherein in the collapsed configuration, the expandable mapping element is sized to be slidably received within an ablation catheter lumen having a diameter of 0.5 millimeters to 1.5 millimeters.

In Example 26, a mapping catheter comprising a shaft having a proximal end and an opposite distal end, and an expandable mapping element attached to the distal end of the shaft and including a plurality of individually-addressable electrodes, the expandable mapping element configured to self-expand from a collapsed configuration to an expanded configuration when extended distally from an ablation catheter lumen, the expanded configuration defined by a proximal portion extending from the distal end of the shaft and forming a proximally-facing concave recess, an intermediate portion extending distally from the proximal portion and defining a maximum diameter of the mapping element when in the expanded configuration, and a distal portion having a conical shape with a distal portion diameter that decreases in a direction distally of the intermediate portion, wherein the electrodes are located in one or both of the intermediate portion and the distal portion.

In Example 27, the mapping catheter of Example 26, wherein the distal end of the shaft is disposed within the concave recess when the expandable mapping element is in the expanded configuration.

In Example 28, the mapping catheter of Example 27, wherein the expandable mapping element is constructed from a plurality of insulated members formed into a braided mesh, the insulated members each including a wire core made of a shape memory alloy, and an insulative covering over the wire core.

In Example 29, the mapping catheter of Example 28, wherein the wire core of each electrode member is electrically conductive and is electrically coupled to an external signal processor, and wherein each electrode is defined by an uninsulated segment of the respective one of the electrode members.

In Example 30, the mapping catheter of Example 29, wherein in the collapsed configuration, the expandable mapping element is sized to be slidably received within an ablation catheter lumen having a diameter of 0.5 millimeters to 1.5 millimeters.

In Example 31, a cryoablation catheter system comprising a cryoablation catheter and a mapping catheter. The cryoablation catheter includes a cryoablation catheter body having a proximal end and a distal end and including a catheter lumen extending therethrough, and a catheter balloon disposed at the distal end of the catheter body. The mapping catheter is configured to be slidably received within the catheter lumen and comprises a shaft having a proximal end and an opposite distal end, and an expandable mapping element attached to the distal end of the shaft. The expandable mapping element includes a plurality of individually-addressable electrodes, and is configured to self-expand from a collapsed configuration when disposed within the catheter lumen to an expanded configuration when extended distally from the catheter lumen. The expanded configuration is defined by a proximal portion extending from the distal end of the shaft and forming a proximally-facing concave recess, an intermediate portion extending distally from the proximal portion and defining a maximum diameter of the mapping element when in the expanded configuration, and a distal portion having a conical shape with a distal portion diameter that decreases in a direction distally of the intermediate portion, wherein the plurality of electrodes are located in one or both of the intermediate portion or the distal portion.

In Example 32, the mapping catheter of Example 31, wherein the expandable mapping element is constructed from a plurality of insulated members formed into a braided mesh, the insulated members including a wire core made of a shape memory alloy, and an insulative covering over the wire core.

In Example 33, the mapping catheter of Example 32, wherein the wire core of each electrode member is electrically conductive and is electrically coupled to an external signal processor, and wherein each electrode is defined by an uninsulated segment of the respective one of the electrode members.

In Example 34, the mapping catheter of Example 33, wherein in the collapsed configuration, the expandable mapping element is sized to be slidably received within an ablation catheter lumen having a diameter of 0.5 millimeters to 1.5 millimeters.

In Example 35, the mapping catheter of Example 34, wherein the plurality of electrodes includes two or more groups of electrodes each positioned at a selected axial location within one or both of the intermediate portion and the distal portion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
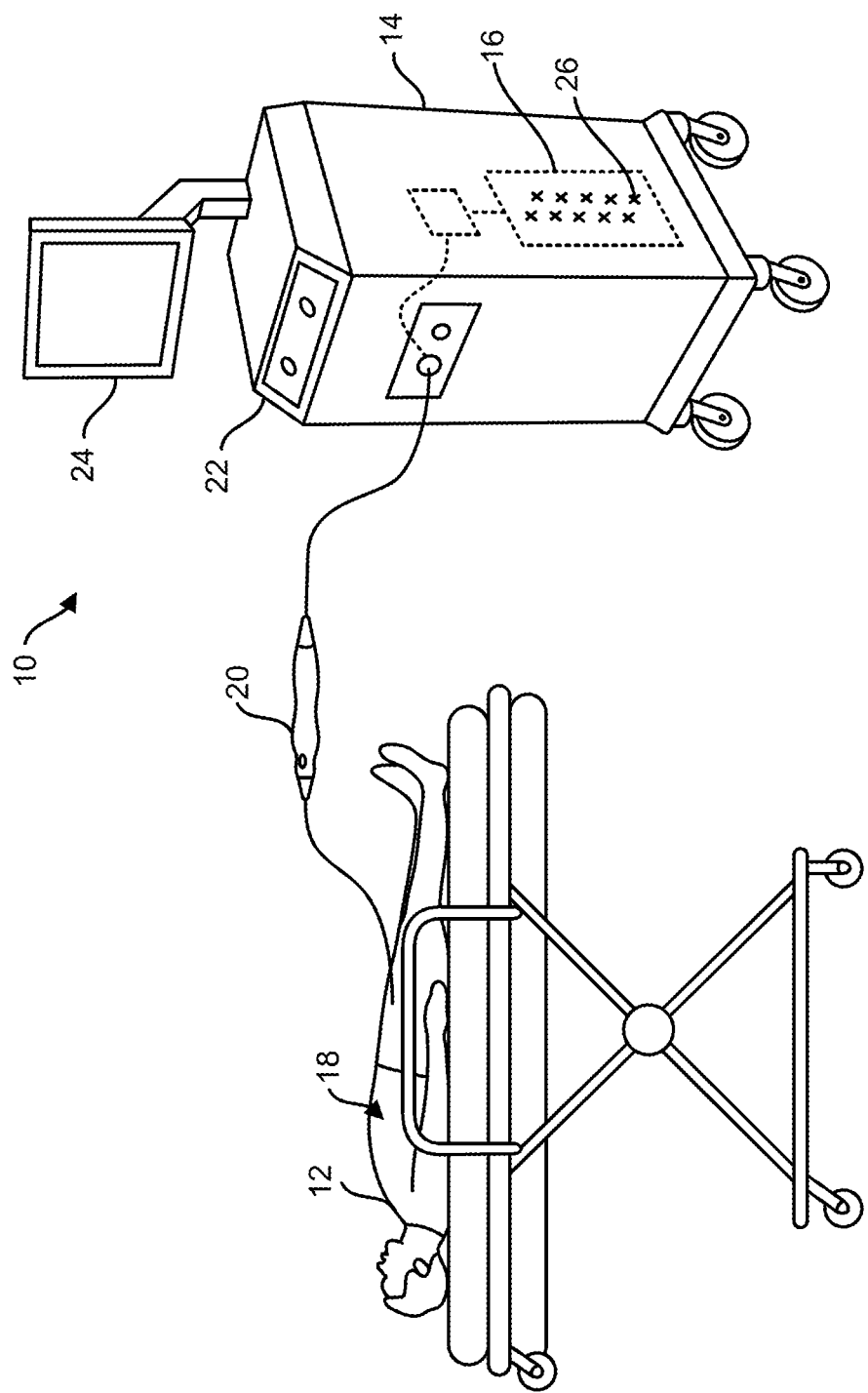
FIG. 1 is a schematic side view illustration of a patient and one embodiment of an intravascular catheter system having features of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic side view of one embodiment of an intravascular catheter system 10 (also sometimes referred to herein as a "catheter system") for use with a patient 12. Although the catheter system 10 is specifically described herein with respect to an intravascular catheter system, it is understood and appreciated that other types of catheter systems and/or ablation systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of an intravascular catheter system is not intended to be limiting in any manner.

The design of the catheter system 10 can be varied. In certain embodiments, such as the embodiment illustrated in FIG. 1, the catheter system 10 can include one or more of a control system 14, a fluid source 16, a balloon catheter 18 including a handle assembly 20, a control console 22 and a graphical display 24. Additionally, as will be explained in greater detail below, the catheter system 10 further includes a high-density mapping catheter (not shown in FIG. 1) that is deployable through the balloon catheter 18 and is configured to sense intrinsic cardiac activation signals to assist the user of the catheter system 10 during the ablation procedure.

It is understood that although FIG. 1 illustrates the structures of the catheter system 10 in a particular position, sequence and/or order, these structures can be located in any suitably different position, sequence and/or order than that illustrated in FIG. 1. It is also understood that the catheter system 10 can include fewer or additional components than those specifically illustrated and described herein.

In various embodiments, the control system 14 is configured to monitor and control the various processes of the ablation procedure. More specifically, the control system 14 can control release and/or retrieval of a cryogenic fluid 26 to and/or from the balloon catheter 18. In certain embodiments, the control system 14 can control various structures described herein that are responsible for maintaining and/or adjusting a flow rate and/or fluid pressure of the cryogenic fluid 26 that is released to the balloon catheter 18 during a cryoablation procedure. In such embodiments, the catheter system 10 delivers ablative energy in the form of cryogenic fluid 26 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18 described herein. Further, or in the alternative, the control system 14 can receive data and/or other information (hereinafter sometimes referred to as "sensor output") from various structures within the catheter system 10. In some embodiments, the control system 14 can assimilate and/or integrate the sensor output, and/or any other data or information received from any structure within the catheter system 10. Additionally, or in the alternative, the control system 14 can control positioning of portions of the balloon catheter 18 within the body of the patient 12, and/or can control any other suitable functions of the balloon catheter 18.

The fluid source 16 contains the cryogenic fluid 26, which is delivered to the balloon catheter 18 with or without input from the control system 14 during the cryoablation procedure. The type of cryogenic fluid 26 that is used during the cryoablation procedure can vary. In one non-exclusive embodiment, the cryogenic fluid 26 can include liquid nitrous oxide. In another non-exclusive embodiment, the cryogenic fluid 26 can include liquid nitrogen. However, any other suitable cryogenic fluid 26 can be used.

The design of the balloon catheter 18 can be varied to suit the specific design requirements of the catheter system 10. As shown, the balloon catheter 18 is inserted into the body of the patient 12 during the cryoablation procedure. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a health care professional (also sometimes referred to herein as an "operator"). As used herein, health care professional and/or operator can include a physician, a physician's assistant, a nurse and/or any other suitable person and/or individual. In certain embodiments, the balloon catheter 18 is positioned within the body of the patient 12 utilizing at least a portion of the sensor output received from the balloon catheter 18. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue. While specific reference is made herein to the balloon catheter 18, as noted above, it is understood that any suitable type of medical device and/or catheter may be used.

The handle assembly 20 is handled and used by the operator to operate, position and/or control the balloon catheter 18. The design and specific features of the handle assembly 20 can vary to suit the specific design requirements of the catheter system 10. In the embodiment illustrated in FIG. 1, the handle assembly 20 is separate from, but in electrical and/or fluid communication with the control system 14, the fluid source 16 and/or the graphical display 24. In some embodiments, the handle assembly 20 can integrate and/or include at least a portion of the control system 14 within an interior of the handle assembly 20. It is understood that the handle assembly 20 can include additional components than those specifically illustrated and described herein.

In the embodiment illustrated in FIG. 1, the control console 22 includes at least a portion of the control system 14, the fluid source 16, and the graphical display 24. However, in alternative embodiments, the control console 22 can contain additional structures not shown or described herein. Still alternatively, the control console 22 may not include various structures that are illustrated within the control console 22 in FIG. 1. For example, in one embodiment, the control console 22 does not include the graphical display 24.

In various embodiments, the graphical display 24 is electrically connected to the control system 14. Additionally, the graphical display 24 provides the operator of the catheter system 10 with information that can be used before, during and after the cryoablation procedure. For example, the graphical display 24 can provide the operator with information based on the sensor output, and any other relevant information that can be used before, during and after the cryoablation procedure. The specifics of the graphical display 24 can vary depending upon the design requirements of the catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time. Further, in various embodiments, the graphical display 24 can include one or more colors, different sizes, varying brightness, etc., that may act as alerts to the operator. Additionally, or in the alternative, the graphical display 24 can provide audio data or information to the operator.

Figure 2:
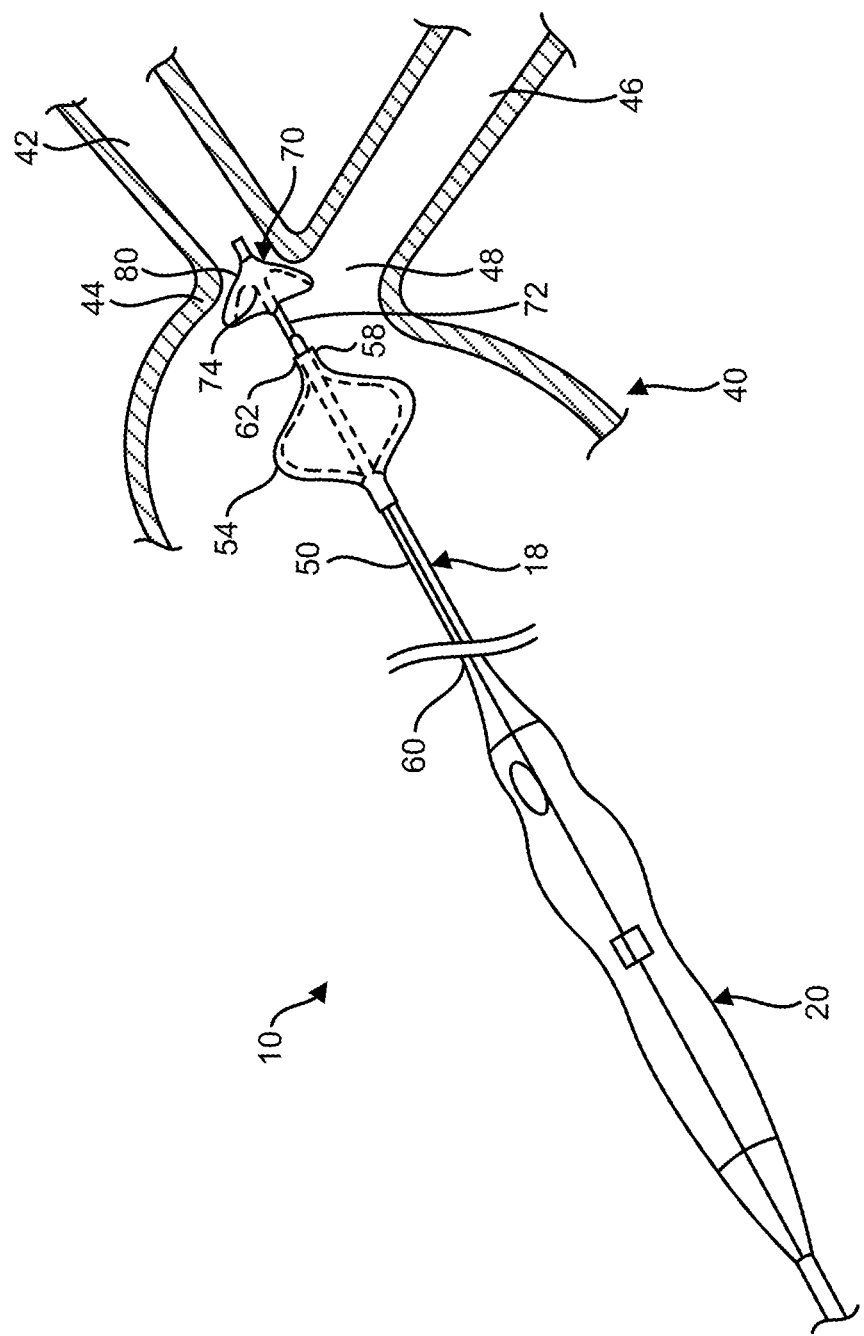
FIG. 2 is a simplified side view of a portion of a patient and a portion of one embodiment of the intravascular catheter system including a balloon catheter and an expandable mapping catheter.

FIG. 2 is a simplified schematic illustration view of a portion of the intravascular catheter system 10 positioned in a left atrium 40 of the patient 12 for use in a pulmonary vein isolation (PVI) procedure to treat atrial fibrillation. As illustrated, a first pulmonary vein 42 extends from the left atrium 40 at an ostium 44, and a second pulmonary vein 46 extends from the left atrium 40 at an ostium 48. As will be readily understood by the skilled artisan, the PVI procedure involves ablating the cardiac tissue proximate the ostium 44 and/or the ostium 48 to form a conduction block to terminate the atrial fibrillation.

As shown, the balloon catheter 18 includes a catheter body 50, a catheter balloon 54 and a guidewire lumen 58. As further shown, the catheter body 50 has proximal end 60 and an opposite distal end 62, and the handle assembly 20 and the catheter balloon 54 are attached, respectively, to the proximal and distal ends 60, 62. Additionally, the catheter balloon 54 is further attached at its distal portion to the guidewire lumen 58. In embodiments, the guidewire lumen 58 is slidably disposed within a main lumen (not illustrated) of the catheter body 50.

The catheter system 10 further includes a mapping catheter 70 extending within and distally from the guidewire lumen 58. As shown, the mapping catheter 70 includes a catheter shaft 72 having a distal end 74, and an expandable mapping element 80 extending from the shaft distal end 74. In the illustrated embodiment, the mapping element 80 is depicted in an expanded state with a portion thereof in contact with the ostium 44 of the pulmonary vein 42. The mapping element 80 is configured to sense, via a plurality of electrodes (not shown in FIG. 2) located thereon, intrinsic cardiac electrical activation signals, or the lack thereof, originating at the cardiac tissue, and to convey those signals to the control system 20 (FIG. 1) for assessing the effectiveness of the ablation procedure in forming a conduction block within the ablated tissue.

In embodiments, the mapping element 80 is formed of a mesh construction, and is configured to self-expand from a collapsed configuration for deployment through the guidewire lumen 58, to the expanded configuration shown in FIG. 2. That is, in use, the mapping catheter 70 can be inserted through the guidewire lumen 58, and upon full advancement of the mapping element 80 from the guidewire lumen 58, the mapping element 80 will automatically expand to its expanded configuration without further action by the user, as a result of the construction of the mapping element 80. The mesh construction of the mapping element 80 further allows the mapping element 80 to be withdrawn back into the guidewire lumen 58 such that the catheter balloon 54 can be positioned at the ablation site (e.g., to apply ablative energy to the target cardiac tissue).

Additionally, the novel configuration of the fully expanded configuration of the mapping element 80 allows the catheter balloon 54 to be positioned in close proximity to the mapping element 80 during use of the mapping catheter 70, while at the same time providing a shape that is complimentary to the target site. The mapping element 80 is also highly conformable, thus allowing a large number of electrodes to be positioned in intimate contact with the target cardiac tissue being sensed.

Figure 3A:
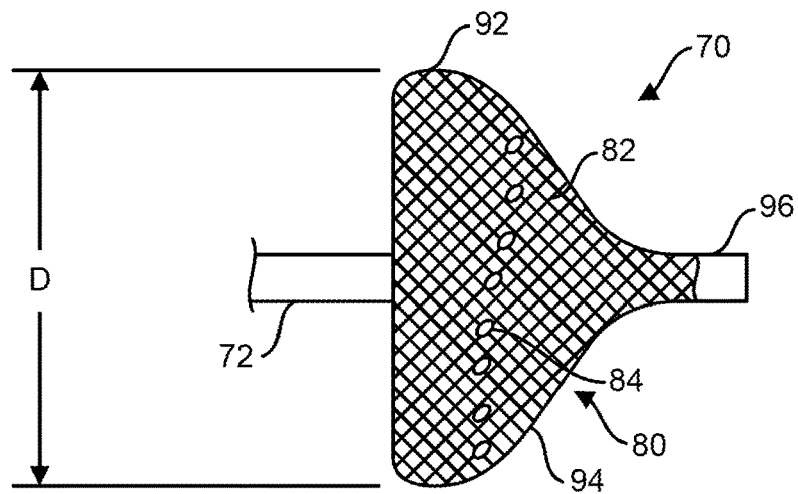
FIGS. 3A-3C are schematic illustrations of portions of the expandable mapping catheter of FIG. 2 according to various embodiments.
Figure 3B:
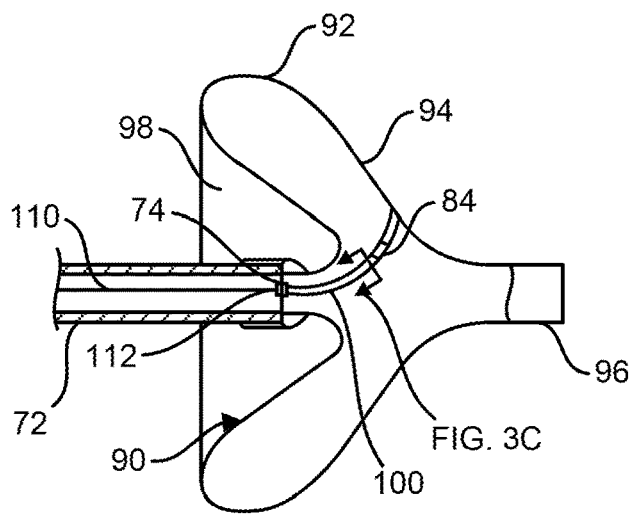
Figure 3C:
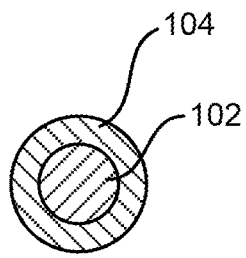

FIGS. 3A and 3B are schematic side and partial cross-sectional views, respectively, of a portion of the mapping catheter 70 in the expanded configuration according to embodiments, while FIG. 3C is a cross-sectional view of a portion of the mapping element 80. The mapping element 80 is formed of a plurality of insulated members 82 that are formed into a braided mesh construction, and includes a plurality of electrodes 84 selectively located on the mapping element 80 so as to be optimally positioned to contact the target cardiac tissue when in use. For purposes of illustrative clarity, only a single insulated member 82 is illustrated in FIG. 3B, and the shape of the mapping element 80 in the expanded configuration is shown in outline so as to clearly illustrate the pre-formed expanded shape of the mapping element 80.

As shown, the shape of the mapping element 80 in the expanded configuration is defined by a proximal portion 90, an intermediate portion 92 and a distal portion 94. As further shown, the mapping element 80 includes a distal tip segment 96, although in other embodiments this segment may be omitted. When present, the tip segment 96 can operate as a cap over the distal extremity of the braid construction of the mapping element 80, to prevent undesired distortion thereof during use and to facilitate pre-forming the mapping element 80 into its expanded configuration shape.

As further shown, the proximal portion 90 extends radially and proximally relative to the distal end 74 of the shaft 72 so as to form a proximally-facing, concave recess 98. The intermediate portion 92 extends distally from the proximal portion 90 and defines a maximum diameter D of the mapping element 80 in the expanded configuration. The distal portion 94 extends distally from the intermediate portion 92 and has, in the expanded configuration, a generally conical shape having a diameter that decreases in the direction distally of the intermediate portion 92. In the illustrated embodiment, the electrodes 84 are located within the distal portion 94. In other embodiments, the electrodes 84 can be located in the intermediate portion 92 in addition to or in lieu of the distal portion 94.

In embodiments, selected ones of the insulated members 82 define electrode members 100, and the individual electrodes 84 are each associated with, e.g., located on, a respective electrode member 100. In addition, as can be seen in FIG. 3C, the illustrated electrode member 100 includes a wire core 102 and an electrically insulative covering 104 over the wire core. In embodiments, the wire core 102 of each electrode member 100 is electrically conductive and is electrically connected to one or more electrical conductors 110 extending within the shaft 72. In the illustrated embodiment, the electrical conductor 110 is connected to the conductive wire core 102 at an interconnect 112. The combination of the electrode 84, wire core 102 and the electrical conductor 110 thus forms an electrical path for conveying sensed cardiac activation signals to the control system 14. In embodiments, the interconnect 112 can take on any form, whether now known or later developed, capable of electrically coupling the wire core 102 and the electrical conductor 110, e.g., crimp connections, weld-bonded connections, and the like.

In the various embodiments, the electrode 84 can be formed in any number of ways. In one embodiment, a segment of the insulative covering 104 is removed (e.g., by ablating the material, by etching, or by mechanical means) to expose the corresponding wire core 102 at the segment, thus forming the electrode 84. In one such embodiment, the exposed wire core 102 at the segment in which the insulating covering 104 has been removed defines the electrode 84. In other embodiments, the electrode 84 may be a separate structure that is mechanically and electrically coupled to the wire core 102 at the location of the removed insulative covering 104.

In still other embodiments, the electrode member(s) 100 on which the respective electrodes 84 are attached operate solely as a support structure, and are not electrically active themselves. For example, in one embodiment, each electrode 84 is mechanically coupled to a corresponding electrode member 100, and a separate electrical conductor is routed to and electrically and mechanically coupled to the electrode 84, e.g., by soldering, crimping, laser melting, and the like.

In various embodiments, the braided expandable mapping element 80 may be formed by a combination of insulated and uninsulated members. That is, although the mapping element of FIGS. 3A-3C has been described as being formed of the insulated members 82 woven into a braided mesh construction, in other embodiments, the mapping element 80 may be formed of a combination of insulated and uninsulated wire members (i.e., bare wire cores). In such embodiments, only the members to which the electrodes 84 are electrically coupled need be wholly or partially insulated.

In the various embodiments, the wire cores 102 forming the insulated members 100 (or uninsulated members, as the case may be) can be formed of materials having sufficient flexibility and shape memory characteristics necessary to form the self-expanding braided mesh. In embodiments, the wire cores 102 may be formed from a nickel titanium alloy (commonly referred to as nitinol), which has excellent shape memory properties and is also highly elastic, enabling a high collapsed-to-expanded size ratio required of the self-expanding mapping element 80. For example, in embodiments, the mapping element 80, in its collapsed configuration, is capable of being advanced through a guidewire lumen 58 having a diameter of about 0.5 millimeters to about 1.5 millimeters, while at the same time expanding to its expanded configuration with a maximum diameter D of between about 20 millimeters and 34 millimeters. In one embodiment, the mapping element 80, in its collapsed configuration, is capable of being advanced through a guidewire lumen 58 having a lumen diameter of one (1) millimeter.

Additionally, the mapping element 80 must also be capable of being re-collapsed to its collapsed configuration, e.g., by retracting the mapping element 80 back into the guidewire lumen 58 to allow for removal of the catheter 18 and/or the mapping catheter 70, or to re-deploy the catheter 18 to a different target site. Super-elastic shape memory alloys such as nitinol exhibit sufficient shape memory and elastic properties to meet these requirements, and are also sufficiently electrically conductive to operate as part of the conductive path for conveying sensed electrical signals to the control system 14.

The insulative covering 104, when present, can be selected from any material having sufficient dielectric strength to provide the necessary electrical insulating functionality at small thicknesses so as to not significantly affect the structural performance of the mesh construction. In embodiments, the insulative covering 104 can be made from a material that is both electrically insulative and also lubricious so as to reduce frictional resistance when advanced through the guidewire lumen 58. In embodiments, the insulative covering 104 may be a fluourocarbon-based material such as ethylene tetrafluoroethylene (ETFE). Other suitable materials for the insulative covering 104 will be apparent to the skilled artisan based on the foregoing.

In general, the mesh-type mapping element 80 allows for the inclusion of a large number of individual electrodes 84 compared to a conventional linear or loop-type mapping catheter such as is currently used in cardiac ablation procedures. The number, size and positioning of the electrodes 84 on the mapping element 80 can depend on the physical constraints of the mapping catheter 70. For example, the number of electrodes 84 may be limited by the number of individual electrical conductors 110 that can be supported by the shaft 72. In embodiments, the mapping element 80 may include between four (4) and 48 electrodes 84 located in the intermediate portion 92 and/or the distal portion 94 of the mapping element 80 when in the expanded configuration. In one embodiment, the mapping element 80 includes 32 electrodes 84 distributed about the distal portion 94 of the mapping element, which is sufficient to provide a high-density electrical map of the target tissue.

In the illustrated embodiment shown in FIG. 3A, the electrodes 84 shown as a circular array of electrodes 84 that are substantially equally spaced about the circumference of the distal portion 94 at substantially the same axial location when the expandable mapping element 80 is in the expanded configuration. However, in other embodiments, the particular locations and distribution of the electrodes 84 can be different than in the illustrative embodiment. For example, the plurality of electrodes 84 can include two or more groups of electrodes 84 each positioned at a different selected axial location within one or both of the intermediate portion 92 and/or the distal portion 94. In one such embodiment, the plurality of electrodes 84 can include a first group of electrodes 84 located in the intermediate portion 92, and second group of electrodes 84 located in the distal portion 94. In embodiments, the electrodes 84 can be distributed in a non-circular pattern, e.g., a helical pattern extending in one or both of the intermediate portion 92 and/or the distal portion 94. In embodiments, the electrodes 84 can be randomly distributed about the mapping element 80. In still other embodiments, the mapping element 80 can include electrodes 84 located within the proximal portion 90. In short, the present disclosure is not limited to any particular locations or distribution of electrodes 84 on the mapping element 80.

In various embodiments, the mapping catheter 70 can advantageously be tracked within the patient's body using an external tracking system via impedance tracking as is known in the art, thus facilitating visualization of the mapping catheter 70, and consequently, the balloon catheter 18, on the display of a three-dimensional electroanatomical mapping system (e.g., the RHYTHMIA® HDx mapping system marketed by Boston Scientific Corporation). This capability can be particularly advantageous for use in the cryoablation catheter system 10, where size constraints of the balloon catheter 18 inhibit the inclusion of separate magnetic tracking sensors.

Various other embodiments of the mapping catheter 70 can further include a 5- or 6-degree-of-freedom magnetic localization element (not shown) at a fixed, known location on the shaft 72 to facilitate tracking of the mapping catheter 70 using magnetic tracking techniques (e.g., such as those provided by the aforementioned RHYTHMIA® HDx electroanatomical mapping system). When so equipped, the mapping catheter 70 can be used to generate high-density electroanatomical maps of the anatomical chamber.

Figure 4A:
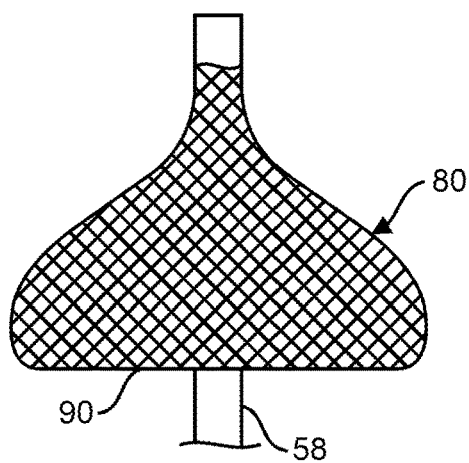
FIGS. 4A-4C depict an expandable mapping element of the mapping catheter of FIG. 2 during various stages of transition from a fully expanded configuration to a collapsed configuration by withdrawing the mapping element into a guidewire lumen of the balloon catheter.
Figure 4B:
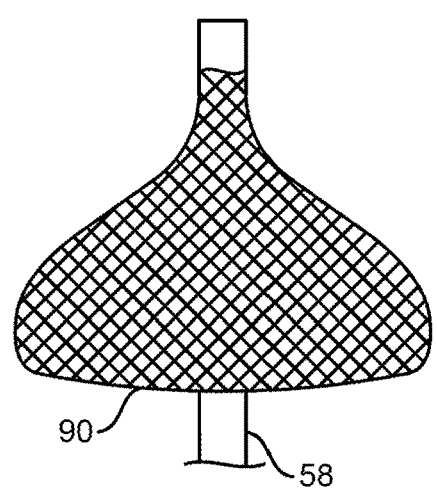
Figure 4C:
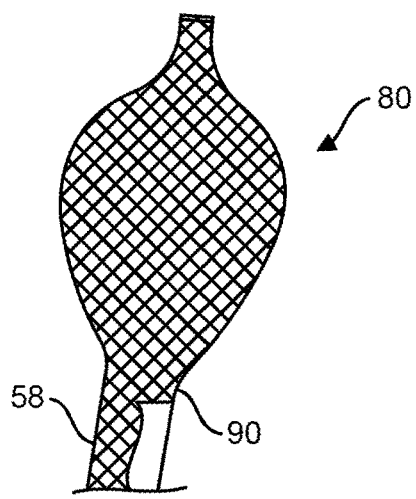

FIGS. 4A-4C depict an expandable mapping element 80 of the mapping catheter 70 during various stages of transition from a fully expanded configuration to a collapsed configuration by withdrawing the mapping element into a guidewire lumen of the balloon catheter. FIG. 4A illustrates the mapping element 80 in its fully expanded configuration, with the distal extremity of the guidewire lumen 58 extending within the concave recess 98 defined by the proximal portion 90. In FIG. 4B, the mapping element 80 has been withdrawn proximally partially within the guidewire lumen 58, and has begun to transition to its collapsed configuration. FIG. 4C illustrates the proximal portion 90 being largely withdrawn into the guidewire lumen 58, such that further retraction will result in the mapping element 80 being fully collapsed (FIG. 4C shows the guidewire lumen 58 in partial cut-away view to better illustrate the retraction of the proximal portion 90 therein). The mesh design of the mapping element 80 facilitates achieving an expanded configuration suitable for mapping a range of pulmonary vein ostia diameters, while still allowing the mapping element 80 to be re-collapsed and re-deployed at a different site.

Figure 5A:
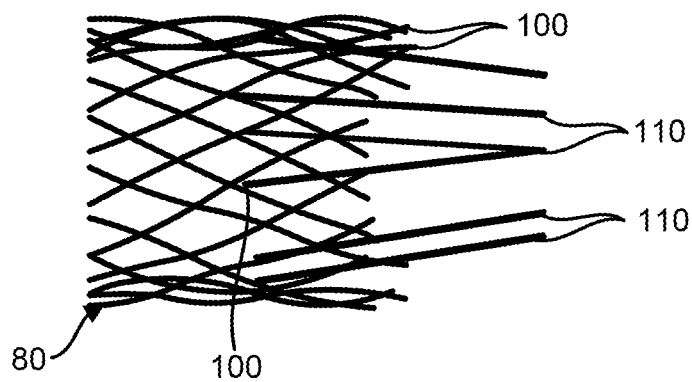
FIGS. 5A-5E are schematic depictions of various techniques for terminating electrical conductors to the mapping element of the mapping catheter of FIG. 2.
Figure 5B:
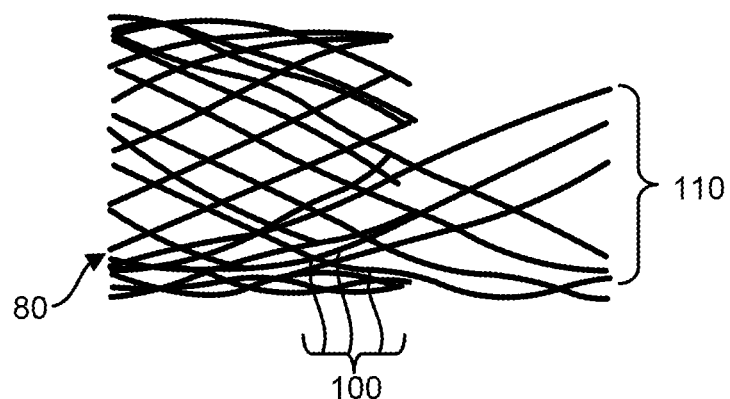
Figure 5C:
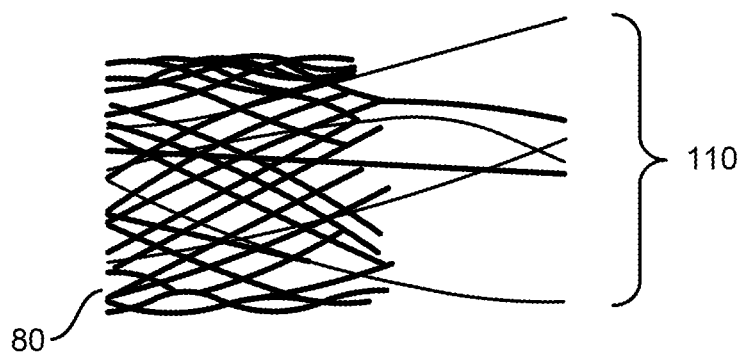

FIGS. 5A-5E are schematic depictions of various techniques for terminating electrical conductors to the mapping element 80, according to various embodiments. In the embodiment of FIG. 5A, a plurality of individual electrical conductors 110 are terminated at respective electrode members 100, and can be electrically and mechanically attached thereto by any suitable means (e.g., solder, brazing, crimping, laser welding, and the like). FIG. 5B illustrates an alternative embodiment in which selected electrode members 100 also operate as the electrical conductors 100. This can be accomplished, for example, by selectively cutting an elongated tubular mesh to define the mapping element 80, while leaving the selected electrode members 100/electrical conductors 110 uncut. FIG. 5C illustrates an embodiment in which individual electrical conductors 110 are routed through the interior of the mapping element to electrode locations (not shown in FIG. 5C), as described elsewhere herein.

Figure 5D:
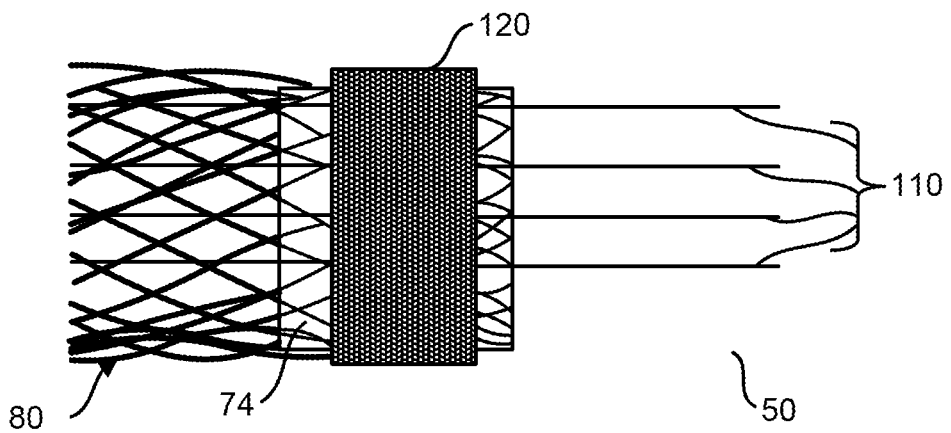

The embodiment of FIG. 5D is an alternate version of the FIG. 5C embodiment, including individual conductors 110 routed along the mapping element 80 to respective electrode locations. As shown in FIG. 5D, in the illustrated embodiment, the shaft distal end 74 is disposed about a proximal end of the mapping element 80, and a crimp band 120 disposed about the shaft distal end 74. In embodiments, the crimp band 120 is operable to mechanically secure the shaft 72 to the mapping element 80.

Figure 5E:
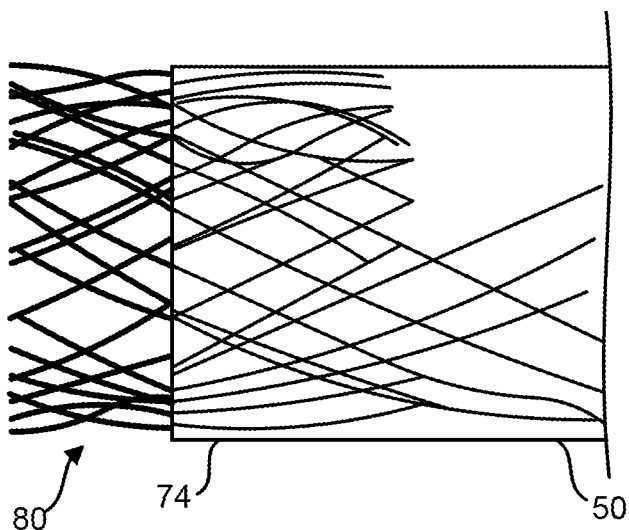

FIG. 5E illustrates an alternative embodiment in which the braided mesh mapping element 80 is embedded, at its proximal end, into the shaft distal end 74 so as to secure the mapping element 80 to the shaft 72. The foregoing can be accomplished, for example, by inserting the tubular braided mesh into the shaft distal end 74 and applying sufficient heat to the assembly to cause the shaft material to reflow and encapsulate the braided mesh.

It is emphasized, however, that the foregoing descriptions for terminating the respective electrical conductors and attaching the mapping element to the shaft are exemplary only, and are not intended to limit in any way the scope of the present disclosure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A mapping catheter comprising:
a flexible shaft having a proximal end and an opposite distal end;
an expandable mapping element attached to the distal end of the flexible shaft, the expandable mapping element comprising:
a plurality of insulated members formed into a braided mesh, the expandable mapping element being configured to self-expand from a collapsed configuration to an expanded configuration when extended distally from an ablation catheter lumen, the expanded configuration defined by a proximal portion extending proximally from the distal end of the flexible shaft and forming a proximally-facing concave recess, an intermediate portion extending distally from the proximal portion and defining a maximum diameter of the mapping element when in the expanded configuration, and a distal portion having a conical shape with a distal portion diameter that decreases in a direction distally of the intermediate portion, the distal portion including a tip segment disposed over a distal extremity of the braided mesh, the tip segment positioned distal to the distal portion, wherein the plurality of insulated members includes a plurality of electrode members,
and wherein the distal end of the flexible shaft is disposed within the concave recess when the expandable mapping element is in the expanded configuration;
a plurality of electrodes located in one or both of the intermediate portion and the distal portion, wherein each of the electrodes is located on a respective one of the electrode members and is configured to sense intrinsic cardiac activation signals in use;
one or more electrical conductors extending within the flexible shaft; and
one or more interconnects electrically coupling the one or more electrical conductors and the plurality of electrode members, and wherein the one or more interconnects is disposed within the flexible shaft, spaced from the braided mesh and within the concave recess when the expandable mapping element is in the expanded configuration.

2. The mapping catheter of claim 1, wherein the insulated members each include a wire core made of a shape memory alloy, and an insulative covering over the wire core.

3. The mapping catheter of claim 2, wherein the wire core of each electrode member is electrically conductive and is electrically coupled to an external signal processor, and wherein each electrode is defined by an uninsulated segment of the respective one of the electrode members.

4. The mapping catheter of claim 2, wherein each of the electrodes is attached to a respective one of the electrode members.

5. The mapping catheter of claim 4, wherein the wire core of each electrode member is electrically conductive and is electrically coupled to an external signal processor, and wherein each electrode is electrically and mechanically connected to a respective one of the electrode members at an uninsulated segment thereof.

6. The mapping catheter of claim 1, wherein the electrodes are equally spaced about the distal portion in a circular pattern when the expandable mapping element is in the expanded configuration.

7. The mapping catheter of claim 1, wherein the plurality of electrodes includes two or more groups of electrodes each positioned at a selected axial location within one or both of the intermediate portion and the distal portion.

8. The mapping catheter of claim 7, wherein the two or more groups of electrodes includes a first group of electrodes located in the intermediate portion, and second group of electrodes located in the distal portion.

9. The mapping catheter of claim 1, wherein the expandable mapping element includes a distal hub portion distal of the distal portion and disposed about the plurality of insulated members.

10. The mapping catheter of claim 9, wherein in the collapsed configuration, the expandable mapping element is sized to be slidably received within an ablation catheter lumen having a diameter of 0.5 millimeters to 1.5 millimeters.

* * * * *